United States Patent
Grant et al.

(10) Patent No.: US 11,684,796 B2
(45) Date of Patent: Jun. 27, 2023

(54) ELECTROMAGNETIC RADIATION TECHNIQUES FOR IN VIVO TISSUE

(71) Applicant: Strathspey Crown, LLC, Newport Beach, CA (US)

(72) Inventors: Robert Edward Grant, Laguna Beach, CA (US); Matthew T. Case, Laguna Hills, CA (US)

(73) Assignee: Crown Holdings, LLC, Newport Beach, CA (US)

( * ) Notice: Subject to any disclaimer, the term of this patent is extended or adjusted under 35 U.S.C. 154(b) by 993 days.

(21) Appl. No.: 16/535,636

(22) Filed: Aug. 8, 2019

(65) Prior Publication Data

US 2019/0381334 A1   Dec. 19, 2019

Related U.S. Application Data

(62) Division of application No. 14/854,935, filed on Sep. 15, 2015, now Pat. No. 10,398,908.

(51) Int. Cl.
*A61N 5/06* (2006.01)
*A61H 23/00* (2006.01)
*A61N 5/067* (2006.01)

(52) U.S. Cl.
CPC .............. *A61N 5/06* (2013.01); *A61H 23/008* (2013.01); *A61N 5/0601* (2013.01); *A61H 2201/10* (2013.01); *A61N 5/067* (2021.08); *A61N 2005/063* (2013.01)

(58) Field of Classification Search
CPC ........ A61N 5/06; A61N 5/0601; A61N 5/067; A61N 2005/063; A61H 23/008; A61H 2201/10; H01J 37/3211
See application file for complete search history.

(56) References Cited

U.S. PATENT DOCUMENTS

| | | |
|---|---|---|
| 4,686,127 A | 8/1987 | Burns et al. |
| 6,024,690 A | 2/2000 | Lee et al. |
| 6,033,357 A | 3/2000 | Ciezki et al. |
| 6,077,213 A | 6/2000 | Ciezki et al. |
| 6,221,094 B1 | 4/2001 | Bare |
| 6,309,339 B1 | 10/2001 | Ciezki et al. |
| 6,521,210 B2 | 2/2003 | Ohkawa |
| 6,626,816 B1 | 9/2003 | Ciezki et al. |
| 6,725,081 B2 | 4/2004 | Ciezki et al. |

(Continued)

OTHER PUBLICATIONS

Dubost, G. and Bellossi, A., "Experimental Approach of the Electromagnetic Effects in Vivo Due to the Solitary-Waves Radiated by a Confined Plasma Antenna", The Second European Conference on Antennas and Propagation, Nov. 11-16, 2007, EuCAP 2007, Publisher: IET.

*Primary Examiner* — Quang D Thanh
(74) *Attorney, Agent, or Firm* — Fish IP Law, LLP

(57) ABSTRACT

A method for using a sonic wave to influence material in a target structure requires using a confined plasma antenna to generate an electromagnetic carrier wave, $\lambda$. The confined plasma antenna also pulses the carrier wave at a sonic frequency, f, to create a sonic wave. In detail, pulsing the carrier wave results in a sequential plurality of solitons which are separated from each other by a periodicity p, wherein $\lambda \ll p$. For the present invention, f is selected to resonate with a material (e.g. a cellular structure) in a target structure (e.g. a patient).

14 Claims, 1 Drawing Sheet

(56) References Cited

U.S. PATENT DOCUMENTS

| | | |
|---|---|---|
| 7,280,874 B2 | 10/2007 | Boehm |
| 7,418,294 B2 | 8/2008 | May |
| 7,500,956 B1 | 3/2009 | Wilk |
| 8,326,408 B2 | 12/2012 | Green et al. |
| 8,440,154 B2 | 5/2013 | Fahs, II et al. |
| 8,591,419 B2 | 11/2013 | Tyler |
| 2005/0203578 A1* | 9/2005 | Weiner .................... A61N 5/00 607/2 |
| 2005/0249667 A1* | 11/2005 | Tuszynski ................ A61N 7/00 424/9.3 |

* cited by examiner

ELECTROMAGNETIC RADIATION TECHNIQUES FOR IN VIVO TISSUE

This application is a divisional application of U.S. patent application Ser. No. 14/854,935 filed on Sep. 15, 2015. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The present invention pertains generally to systems and methods for generating, in combination, an electromagnetic wave having a wavelength $\lambda$ and a sonic wave having a frequency f, for simultaneous transmission of these waves on a same beam path for incidence on a target structure. More particularly, the present invention pertains to systems and methods that pulse an electromagnetic carrier wave at a controlled sonic frequency f to create solitons on the carrier wave. The present invention is particularly, but not exclusively, useful as a system and method for influencing material in a target with a sonic wave, when the sonic wave is created by solitons that are carried on an electromagnetic wave and the frequency f of the sonic wave is selected to resonate with a specified material in the target structure.

BACKGROUND

The following description includes information that may be useful in understanding the present invention. It is not an admission that any of the information provided herein is prior art or relevant to the presently claimed invention, or that any publication specifically or implicitly referenced is prior art.

Electromagnetic waves and sonic waves are both well known. From a very simplistic perspective, although both wave types will radiate through a medium and can be characterized by a periodicity, they otherwise have very profound differences. Interestingly, they are referred to by different physical characteristics. For instance, electromagnetic waves (e.g. light wave) are typically identified by their wavelength, $\lambda$ (i.e. their period). On the other hand, though sonic waves also have a period, sonic waves are typically identified by their frequency, f (i.e. period/time). In comparison, a wavelength $\lambda$ for light is very much less than the period p of a sonic wave ($\lambda \ll p$).

Insofar as wave types are concerned, of interest for the present invention is a physical phenomenon known as a solitary-wave, or soliton. A soliton is a very specific type of self-reinforcing waveform that has several unique characteristics. Technically, these characteristics can result when non-linearity and dispersion effects, on a wave that is traveling in a medium, interact with (i.e. cancel) each other. The characteristics of a soliton include: a constant shape that does not change over time; a constant energy (self-reinforcing); and a localized effect within a region. Of particular interest for the present invention are solitons that are created on a wave of electromagnetic radiation.

An example of a device for generating solitons (solitary-waves) on an electromagnetic wave is provided in an article by G. Dubost and A. Bellossi entitled "Experimental Approach of the Electromagnetic Effects In Vivo due to the Solitary-Waves Radiated by a Confined Plasma Antenna" which was published November 2007, at The Second European Conference on Antennas and Propagation (pages 1-5, Conference on Nov. 11-16, 2007). The Dubost/Bellossi article further discloses the observation that electromagnetic waves can interact with the amplitude of electric fields in surface waves (e.g. Zeneck waves) on a living medium for in vivo reradiation of the electromagnetic waves by nervous fibers.

In addition to the above, it is also known that various waveforms, both light waves and sonic waves, are capable of influencing matter. In particular U.S. patent application Ser. No. 14/488,101, filed on Sep. 16, 2014 for an invention entitled "System and Method for Using Sonic Radiation to Influence Cellular Structure", and U.S. patent application Ser. No. 14/632,941, filed on Feb. 26, 2015 for an invention entitled "System and Method for Using Electromagnetic Radiation to Influence Cellular Structure", both of which are assigned to the same assignee as the present invention, provide respective disclosures for using waveforms to influence matter.

With the above in mind, it is an object of the present invention to generate an electromagnetic/sonic-soliton wave for the purpose of influencing matter (e.g. a cellular structure). Another object of the present invention is to provide a system and method for influencing material in a target with a sonic wave, when the sonic wave is created by a plurality of solitons having a frequency f, when the sonic wave is carried on an electromagnetic wave, and the frequency f of the sonic wave is selected to resonate with a specified material in the target structure. Still another object of the present invention is to provide a system and method for influencing material in a target with an electromagnetic/sonic-soliton wave that is easy to implement, is simple to operate and is comparatively cost effective.

SUMMARY OF THE INVENTION

In accordance with the present invention, a system for using electromagnetic radiation to generate sonic waves for the purpose of influencing target material (e.g. a cellular structure) includes, in combination, a confined plasma antenna, a waveguide, and a modulator. In detail, the confined plasma antenna is used for generating a sequential plurality of solitons. For the present invention, each soliton in the plurality is generated as a pulse on an electromagnetic carrier wave having a wavelength $\lambda$. Importantly, each soliton has a constant shape and they all are generated by the confined plasma antenna at a controlled frequency f. Further, the controlled frequency f is a sonic frequency. The result is the creation of an Electronic/Sonic-Soliton wave (sometimes hereinafter referred to as an E/S-S wave).

In its combination with the confined plasma antenna, the waveguide is provided to direct the plurality of solitons as a sonic wave carried by the electromagnetic carrier wave along a beam path toward a target. As envisioned for the present invention, the waveguide can be of any type well known in the pertinent art. For instance, when the electromagnetic carrier wave is a laser beam having the wavelength $\lambda$, the waveguide may be an optical fiber. Another possibility is that the waveguide may be a directional antenna.

The modulator, which is connected directly with the confined plasma antenna, is provided to establish and control operational parameters for the E/S-S wave, such as f and $\lambda$. Specifically, the parameters for f and $\lambda$ are selected to influence material in the target. As envisioned for the present invention, f will typically be a resonant frequency of a material in the target. Further, when the target is a living body (e.g. a patient) $\lambda$ will typically be established by the modulator based on the frequency and electric field amplitude of selected surface waves on the target.

A methodology for generating sonic waves using electromagnetic radiation in accordance with the present invention requires creating a beam of electromagnetic radiation having a wavelength λ. Specifically, the beam of electromagnetic radiation is created for use as a carrier wave. Next, the carrier wave (i.e. the electromagnetic radiation beam) is pulsed at a controlled frequency f to generate a plurality of solitons on the carrier wave. In this case, each soliton will have a constant shape and the controlled frequency f will be a sonic frequency. Then, the plurality of solitons is directed as a sonic wave along a beam path of the carrier wave toward a target. As a setup, operational parameters for f and λ are established to influence material in the target.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION

Figure 1:
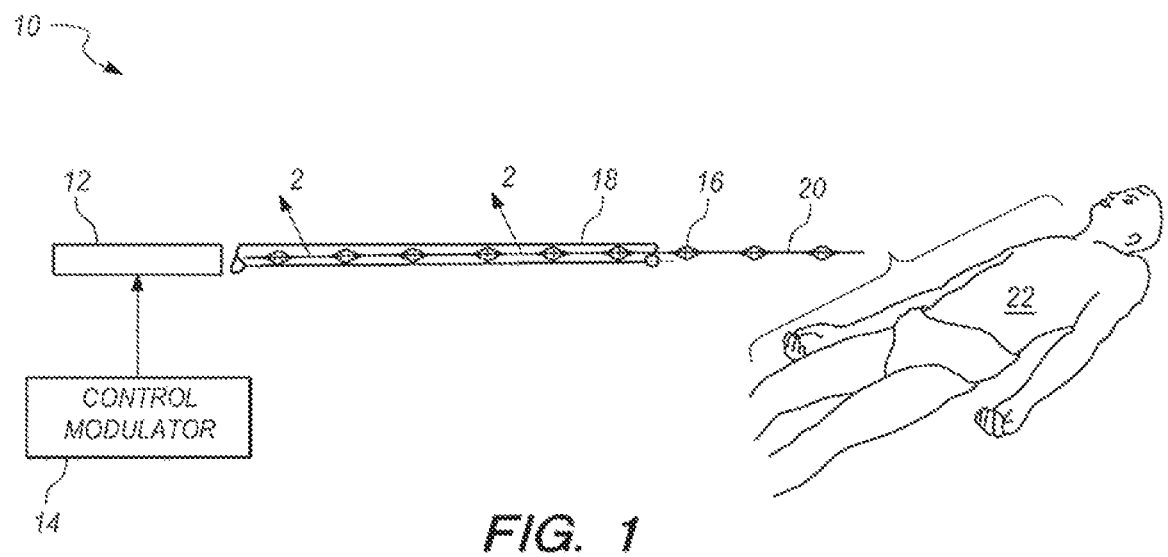
FIG. 1 is a schematic presentation of the components of the present invention in their intended operational environment.

Referring initially to FIG. 1, a system in accordance with the present invention is shown and is generally designated 10. As shown, the system 10 includes a confined plasma antenna 12 which is controlled by a modulator 14 to generate an electromagnetic/sonic-soliton beam 16. Further, the system 10 can optionally include a waveguide 18 which will direct the electromagnetic/sonic-soliton beam 16 along a beam path 20 toward a target, such as the patient 22. As envisioned for the present invention, the waveguide 18 can be of any type well known in the pertinent art. For instance, when the ES-S wave 16 incorporates a laser as its the carrier, the waveguide 18 may be an optical fiber. In any event, as indicated in FIG. 1, the waveguide 18 is intended to have the capability of radiating all, or selected portions, of the target (patient 22).

Figure 2:
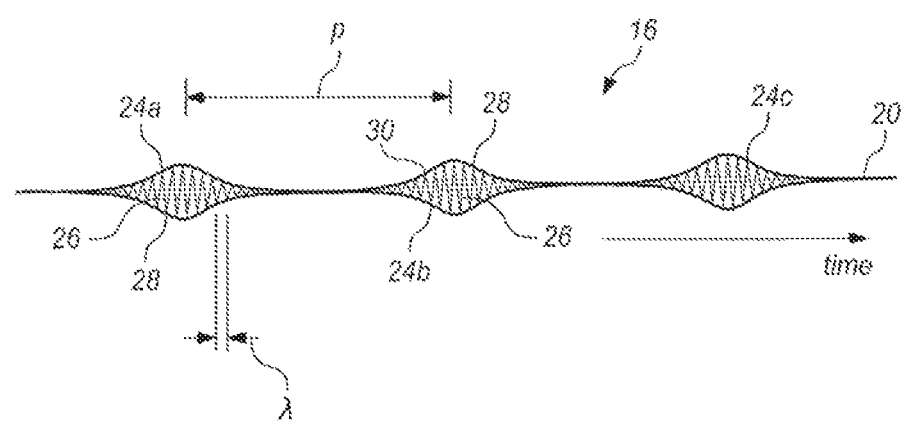
FIG. 2 is a cross-section view of the electromagnetic/sonic-soliton beam generated in accordance with the present invention.

As shown in FIG. 2, an electromagnetic/sonic-soliton beam 16 is shown to include a plurality of solitons 24, of which the solitons 24a, 24b and 24c are exemplary. Further, it will be seen that the electromagnetic/sonic-soliton beam 16 is based on an electromagnetic radiation 26 which has a wavelength λ, and effectively acts as a carrier for a sonic wave 28.

Operationally, the sonic wave 28 is created by pulsing the electromagnetic wave 26 at a sonic frequency f, prior to a radiation of the electromagnetic/sonic-soliton beam 16 from the confined plasma antenna 12. As intended for the present invention, pulsing of the electromagnetic wave 26 is accomplished with a periodicity p for the sonic frequency f. As indicated in FIG. 2, λ is very much shorter than p. The result of all this is that each soliton is contained within a defining envelope 30 that effectively acts as a sonic wave 28. Thus, each soliton 24, in sequence with other solitons 24, can be directed onto a target/patient 22 to influence material (e.g. cellular structure) in the target/patient 22 as the sonic wave 28.

What is claimed is:

1. A method for generating sonic waves using electromagnetic radiation which comprises the steps of:
   creating a beam of electromagnetic radiation having a wavelength λ, wherein the beam of electromagnetic radiation is created for use as a carrier wave;
   pulsing the carrier wave of the electromagnetic radiation beam at a
   controlled frequency f to generate a plurality of solitons on the carrier wave, wherein each soliton has a constant shape and the controlled frequency f is a sonic frequency;
   directing the plurality of solitons as a sonic wave along a beam path of the carrier wave toward a target; and
   establishing operational parameters for the controlled frequency f and the wavelength λ to influence a material in the target.

2. The method of claim 1 wherein the creating step is accomplished using a confined plasma antenna.

3. The method of claim 1 wherein the beam of electromagnetic radiation is a laser beam having the wavelength λ.

4. The method of claim 1 wherein the wavelength λ is established based on a frequency and an amplitude of an electric field of a surface wave on the target.

5. The method of claim 1 wherein an amplitude for solitons in the sonic wave is fixed in the establishing step.

6. The method of claim 1 wherein the controlled frequency f is a resonant frequency of the material in the target.

7. The method of claim 1 wherein the directing step is accomplished using a waveguide.

8. The method of claim 1 wherein the target is tissue in a cellular structure.

9. The method of claim 1, comprising providing a modulator connected to a confined plasma antenna and using the modulator to establish the operational parameters for the controlled frequency f and the wavelength λ.

10. A method for radiating a target with a sonic wave which comprises the steps of:
    determining a frequency f, wherein the frequency f is a characteristic frequency of the target, and
    wherein the frequency f is a sonic frequency having a period p; generating a beam of electromagnetic radiation for use as an electromagnetic carrier wave, wherein the electromagnetic carrier wave has a wavelength λ, and wherein the wavelength λ is smaller than the period p;
    pulsing the electromagnetic carrier wave at the frequency f to create a
    plurality of solitons on the electromagnetic carrier wave, wherein each soliton has a constant shape and wherein the plurality of solitons collectively constitute the sonic wave; and
    directing the sonic wave onto the target.

11. The method of claim 10 wherein the generating step is accomplished using a confined plasma antenna.

12. The method of claim 10 wherein frequency f is a resonant frequency of a material in the target.

13. The method of claim 10 wherein the beam of electromagnetic radiation is a laser beam having the wavelength λ.

14. The method of claim 10 wherein the wavelength λ is based on a frequency and an amplitude of an electric field of a surface wave on the target.

\* \* \* \* \*